United States Patent [19]
Sachdeva et al.

[11] Patent Number: 5,697,779
[45] Date of Patent: Dec. 16, 1997

[54] TEMPORARY IMPLANT FOR USE AS AN ANCHOR IN THE MOUTH

[75] Inventors: Rohit Chaman Lal Sachdeva, Plano, Tex.; Farrokh Farzin-Nia, Inglewood, Calif.

[73] Assignee: Ormco Corporation, Orange, Calif.

[21] Appl. No.: 480,836

[22] Filed: Jun. 7, 1995

[51] Int. Cl.⁶ .................................................. A61C 8/00
[52] U.S. Cl. .......................... 433/2; 233/24; 233/173
[58] Field of Search .................... 433/2, 173, 24, 433/174, 175, 176

[56] References Cited

U.S. PATENT DOCUMENTS

| | | | |
|---|---|---|---|
| 4,011,602 | 3/1977 | Rybicki | 3/1.9 |
| 4,040,129 | 8/1977 | Steinemann et al. | 3/1.9 |
| 4,468,201 | 8/1984 | Fukuyo | 433/176 |
| 4,988,292 | 1/1991 | Rosen | 433/8 |
| 5,015,186 | 5/1991 | Detsch | 433/173 |
| 5,052,930 | 10/1991 | Lodde et al. | 433/173 |
| 5,066,224 | 11/1991 | Block et al. | 433/7 |
| 5,108,289 | 4/1992 | Fukuyo | 433/173 |
| 5,174,755 | 12/1992 | Fukuda | 433/173 |
| 5,192,303 | 3/1993 | Gatturna et al. | 606/75 |

OTHER PUBLICATIONS

"Impaction Posts, A Mechanical Aid to Suturing" Instruction Booklet.

*Primary Examiner*—Edgar S. Burr
*Assistant Examiner*—Dave A. Ghatt
*Attorney, Agent, or Firm*—Wood, Herron & Evans, L.L.P.

[57] ABSTRACT

This invention is directed to a temporary implant for use as an anchor in the mouth, as well as to a method of attaching the temporary implant to the maxillary or mandibular bone. The temporary implant includes an implant adapted to be temporarily affixed in a buccal, labial, lingual or palatal bone surface of the maxillary jawbone, or buccal, labial or lingual bone surface of the mandibular jawbone. In one embodiment, the implant includes a longitudinal threaded cylindrical bore for releasably attaching various orthodontic appliances to the implant.

46 Claims, 3 Drawing Sheets

TEMPORARY IMPLANT FOR USE AS AN ANCHOR IN THE MOUTH

FIELD OF THE INVENTION

This invention relates to the use of an implant in the mouth as an anchor, and more particularly to a temporary implant positioned in a nonocclusal surface of the maxillary or mandibular jawbone.

BACKGROUND OF THE INVENTION

In traditional tooth movement, orthodontic brackets are placed on the teeth, and the brackets are connected to one another using an orthodontic archwire. The orthodontic archwire transfers tooth-moving forces to certain teeth, using other teeth as anchors. However, this traditional method of tooth movement has several potential shortcomings or drawbacks associated with it. For example, in some patients, the tooth or teeth to be used as an anchor may be missing. Furthermore, although a particular tooth may be serving as an anchor in generating an orthodontic force, in reality the teeth being moved also will exert a counter-force on this "anchor" tooth which may cause undesirable movement of the anchor tooth.

Therefore, in treating many orthodontic patients, it is desirable to stabilize certain teeth which otherwise would move due to the reactive forces created in the mouth. Traditionally, this tooth stabilization, or differential tooth movement, has been achieved by applying lower forces in the mouth or by utilizing several teeth as the anchor. However, when lower forces are applied, orthodontic treatment requires significantly more time, and when several teeth are used in combination as an anchor, the resulting tooth-moving response may be somewhat unpredictable. Orthodontists also have used headgear as a way of obtaining differential tooth movement. However, because the headgear is uncomfortable and highly visible, this device has low patient appeal and orthodontists have a difficult time gaining patient compliance.

More recently, it has been proposed to use a permanent implant embedded vertically in the occlusal surface of a jawbone to generate a tooth-moving force. For example, U.S. Pat. No. 4,988,292 teaches the use of an abutment for orthodontic anchorage to a dental implant which is embedded vertically in an edentulous site in the jawbone. The abutment may be used to support any one of a variety of orthodontic attachments, such as hooks and molar tubes. Furthermore, the abutment is intended to be part of a dental restoration plan for a patient who is molar-edentulous. Presumably, when the desired tooth movement has been achieved, the orthodontic abutment may be removed from the dental implant which is vertically embedded in the bone, and a prosthesis may be attached to the implant.

In addition, U.S. Pat. No. 5,015,186 teaches an orthodontic prosthetic head having an orthodontic bracket, wherein the prosthetic head is removably attached to an artificial root implant embedded vertically in the occlusal surface of a jaw in place of a natural tooth. The '186 patent teaches that, because the implant fuses with bone, it can be used as an anchor for applying orthodontic forces on crooked teeth when posterior or back teeth cannot be used due to their absence or due to bone loss adjacent to the back teeth.

In addition to the permanent implants discussed above, it also has been proposed to use a temporary orthodontic implant positioned vertically in the occlusal surface of a jaw. More specifically, it has been proposed to use a retromolar implant as an intraoral anchor in mesially translating second and third molars to eliminate an edentulous first molar space, instead of filling the space with a denture or prosthesis, or using headgear as an extraoral anchor. Dr. W. Eugene Roberts, "Orthodontics as a Restorative Option: Implant Anchorage to Close Posterior Extraction Sites", *Orthodontic Dialogue*, Vol. 7, No. 1, pp. 2–4 (Fall, 1994). This article teaches the placement of an anchorage implant about 5 mm distal to the third molar. After the implant has been affixed in the jawbone for about four months, it may be used as an anchor in stabilizing the pre-molar anterior to the extraction site, by forming a closed loop in the end of an archwire and securing the wire to the implant using a cover screw. At the end of active treatment, the implant may be removed under local anesthesia.

Although the implants discussed above provide an anchor in the mouth for selectively moving teeth, these implants have several limitations. For example, because each of these implants is embedded vertically into the occlusal surface of a jawbone, it must be adapted to withstand severe mastication (chewing) forces of up to about 70 kg. In order to withstand such forces, the implant must be fairly sizable, and must be embedded relatively deeply into the jawbone. Furthermore, because significant bone integration is required for implant stability, a clinician typically must wait from about three to nine months once the bare implant has been installed before the implant may be used in generating tooth moving forces. In addition, given the size of these implants, a clinician is extremely limited in selecting a site in the mouth for embedding the implant. These implants are designed to be embedded either at the site of a missing tooth or distal to the third molar. Moreover, because these implants require a significant amount of bone integration for proper stability, it is relatively difficult to remove such implants after treatment.

Therefore, it would be beneficial to have a temporary implant for use as an anchor in the mouth that can be used immediately or within a few weeks of installation in the mouth. It also would be desirable to have an implant which does not require an edentulous site for implant placement. Furthermore, it would be advantageous to have an implant which does not require significant bone integration, and which may be removed relatively easily once treatment is completed. And in addition, it would be desirable to have an implant that is not particularly susceptible to the mastication forces normally encountered by the occlusal surfaces of the teeth and jawbones in the oral cavity.

SUMMARY OF THE INVENTION

In its broadest aspects, the invention is directed to a temporary implant for use as an anchor in the mouth, as well as to a method of attaching the temporary implant to the maxillary or mandibular bone.

More particularly, the temporary implant includes an implant adapted to be temporarily affixed in a bone surface selected from the group consisting of the buccal, labial, lingual and palatal surfaces of the maxillary jawbone and the buccal, labial and lingual surfaces of the mandibular jawbone. Furthermore, when the implant is affixed in the buccal, labial or lingual surface, it preferably is affixed at an angle of at least about 45° relative to the normal vertical orientation plane of the teeth (hereinafter "vertical orientation plane"). The implant also may include a securing section for releasably attaching an orthodontic appliance to the implant. When an orthodontic appliance is used in conjunction with the temporary implant, the orthodontic appliance may include a fastening section for releasably attaching the appliance to the implant. The appliance may be attached to the implant in a number of different ways. For example, the implant may include a threaded bore with the appliance having a corresponding threaded post, or the implant may include a threaded post, with the appliance having a threaded bore. Alternatively, the two components may snap-fit together or use any other suitable type of releasable attachment mechanism or device. Furthermore, if desired, the temporary implant and orthodontic appliance may be formed as a single component, with the appliance integral with the implant.

Various orthodontic appliances are suitable for use in conjunction with the temporary implant of the invention. For example, the temporary implant may be used in conjunction with a bracket, hook, ball joint, buccal tube, Herbst appliance, arch-expanding jackscrew or the like.

In a preferred form, the temporary implant includes a peripheral flange integral with the outer end (distal from the implanted end), which may be grasped during attachment of an orthodontic appliance to the implant so as to prevent rotation of the implant in the bone once the implant has been temporarily positioned in the bone. If desired, the implant also may include a surface projection extending outwardly from the bone-contacting surface of the implant. The surface projection is adapted to form a slight mechanical interlock with the bone once the implant has been inserted into the bone and may be oriented in any of a number of different ways. For example, a projection aligned parallel to the longitudinal axis of the implant will inhibit relative rotation of the implant within the bone, while a projection aligned perpendicular to the longitudinal axis will inhibit the implant from being pulled out of the bone unintentionally. The surface projection may be of any form, with some examples including annular rings, screw threads, fins or the like.

In one particular embodiment of the temporary implant, the securing section includes a longitudinal bore which extends from the outer end (distal to the implanted end) of the implant to the inner end (proximal to the implanted end) of the implant, and which is adapted to receive a fastening section of an orthodontic appliance. The implant further includes a transverse slit extending longitudinally from the inner end of the implant, whereby insertion of the fastening section into the bore causes the diameter of a portion of the inner end of the implant to expand, thereby securing the implant in the maxillary or mandibular bone.

The implant may be made of a metal, a ceramic, a bioresorbable material such as a polyglycolic acid derivative or poly L-lactate, or any combination of these materials. Preferred metals include titanium, titanium based alloys, nickel-titanium alloys, zirconium and zirconium alloys. In particular, shape memory alloys can be used which are adapted to be in a deformed orientation at ambient mouth temperature, thereby securing the implant to the maxillary or mandibular bone. Preferred ceramics include aluminum oxide, titanium nitride, titanium dioxide, zirconium oxide and calcium phosphate.

With respect to size, due to the placement of the implant in a nonocclusal bone surface of the jawbone and its lack of susceptibility to mastication forces, the implant may be relatively small. For example, the implant typically has a length of from about 2 mm to about 5 mm and a diameter of from about 0.5 mm to about 3 mm.

In the method of attaching the temporary implant, a portion of the implant is inserted into the buccal, labial, lingual or palatal bone surface. When the implant is inserted into the buccal, labial or lingual surface, it preferably is inserted into the bone at an angle of at least about 45° relative to the vertical orientation plane, whereby the implant may be used as a temporary anchor in the mouth. Although the angle is preferably at least about 45°, more preferably, the implant is inserted into the bone at an angle between about 45° and 90° relative to the vertical orientation plane, with a most preferred angle being about 90°. Furthermore, in a preferred form, the implant is inserted about 2 mm to about 3 mm into the bone.

The temporary implant of this invention offers several benefits and advantages over the traditional implants embedded vertically in the occlusal surface of a jawbone. For example, because the temporary implant is not positioned in the occlusal surface, it is subjected to significantly lower chewing forces. Therefore, a smaller, much less invasive implant may be used if desired. Furthermore, it is believed that the implant only needs to be inserted about 2–3 mm into the bone for most treatments, and because little to no bone integration is required for most applications, the temporary implant is ready to use either immediately or within a few weeks after implantation. Also, because the implant is designed to have little bone integration, it is significantly easier to remove after treatment is completed. Additionally, because the temporary implant is installed in the buccal, labial, lingual or palatal surface of the maxillary jaw or the buccal, labial or lingual surface of the mandibular jawbone, as opposed to the occlusal surface of the bone, the clinician is not limited to placing the implant in an edentulous site.

These and other benefits and advantages will become readily apparent to persons skilled in the art upon review of the following Figures and detailed description of the invention.

DETAILED DESCRIPTION OF THE INVENTION

Figure 1:
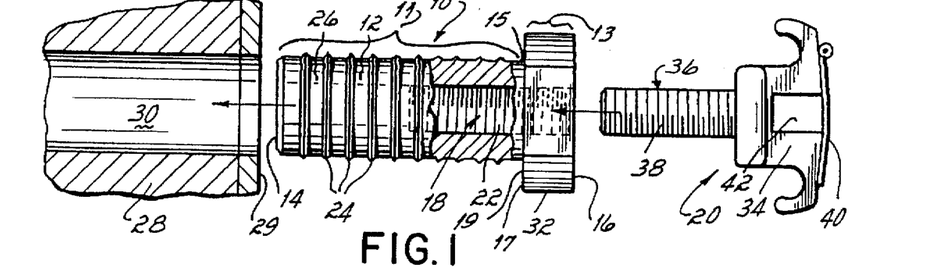
FIG. 1 shows one embodiment of the temporary implant and a corresponding orthodontic appliance; the implant and appliance are adjacent to a hole drilled in a portion of a jawbone.

The temporary implant according to the principles of the invention may be configured in any of a number of different ways and formed from any of a number of different materials, so long as the implant is adapted to be temporarily affixed in a nonocclusal surface of the maxillary or mandibular bone. For example, as shown in FIG. 1, one embodiment of the implant 10 includes a body 12 having an inner end 14, outer end 16 and securing section 18 for releasably attaching an orthodontic appliance 20 to the implant 10. In this particular embodiment, the securing section 18 is a threaded cylindrical bore 22 extending into the interior of the implant body 12 along the longitudinal axis from the implant outer end 16. The implant 10 shown further includes annular ridges 24 on the outer body surface 26 which are adapted to provide a slight mechanical retentive force with the surrounding bone 28 of the maxillary or mandibular jaw once the implant 10 has been placed into an opening 30 in the bone 28. In this particular implant, the outer end 16 includes an enlarged head 32 which is integral with the body portion 12 of the implant 10. Once the implant 10 has been inserted into the bone 28, this enlarged head 32 functions as a gripping surface which may be gripped by a pair of pliers or a dedicated implant-gripping instrument when an orthodontic appliance, such as the orthodontic appliance 20 shown in FIG. 1 for example, is being releasably attached to or removed from the temporary implant 10. By gripping the installed implant in this fashion, various orthodontic appliances may be readily attached or removed without having the implant itself rotate within the bone. The orthodontic appliance 20 shown in FIG. 1 includes an orthodontic bracket 34 and a fastening section 36 integral with the bracket 34. In this particular embodiment, the fastening section 36 is a threaded post 38. Also, the bracket 34 includes a hinge cap 40 which may be snapped over the archwire slot 42 once an archwire (not shown) is placed in the slot 42.

Figure 8:
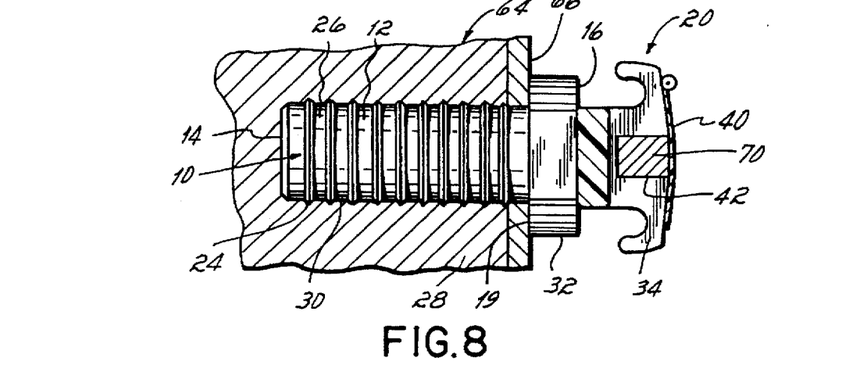
FIG. 8 is a partial cross-section taken along line 8—8 of FIG. 7, showing the temporary implant embedded in the lingual surface of the mandibular jawbone.

The implant 10 shown in FIG. 1 (as well as numerous other embodiments of the invention) also may be described in somewhat different terms. For example, the body 12 may be described as an elongated body 12, with the elongated body 12 having an in-bone portion 11 connected to an above-bone portion 13. By viewing FIG. 1 in conjunction with FIG. 8, it is easy to see how, when the implant 10 is positioned in an opening or hole 30 in the bone 28, the in-bone portion 11 is disposed below the bone surface 29, 66, while the above-bone portion 13 is disposed above the bone surface 29, 66. In this particular embodiment, the above-bone portion 13 is the same as the portion of the body 12 which includes the enlarged head 32. The in-bone portion 11 and the above-bone portion 13 each have an inner and outer end (in-bone 14, 15; above-bone 16, 17), with the cross-sectional area of the above-bone portion inner end 17 being greater than the cross-sectional area of the in-bone portion outer end 15, thereby forming a shoulder 19 having a bone-contacting surface on the above-bone portion inner end 17. When the implant 10 is positioned in an opening in the bone, such as shown in FIG. 8, the shoulder 19 rests on a part of the bone surface adjacent the opening in the bone, such as the lingual surface 66 adjacent the hole 30.

As shown in FIG. 1, the temporary implant 10 is ready for insertion into a hole 30 drilled in a portion of the buccal, labial, lingual or palatal surface of the maxillary jawbone 28 or the buccal, labial or lingual surface of the mandibular jawbone 28. When the implant is inserted into a buccal, lingual or labial surface, it preferably is inserted at an angle of at least about 45° relative to a vertical orientation plane. As used herein, the term "vertical orientation plane" refers to the normal occlusal/gingival or vertical orientation plane of the teeth. Also, as used herein, "buccal" refers to surfaces facing the cheeks, "labial" refers to surfaces facing the lips, "palatal" refers to the surface of the roof of the mouth, and "lingual" refers to surfaces facing the tongue other than the palatal surface. Furthermore, "occlusal" refers to those surfaces of the maxillary and mandibular jawbones which oppose each other when the jaws are closed, and from which the teeth extend in a normal dentition.

Because the temporary implants of this invention are for use in the nonocclusal surfaces (buccal, labial, lingual and palatal) of the maxillary and mandibular jawbones, they are not subject to the traditional heavy loads of as much as 70 kg or more which are placed on traditional occlusal implants due to chewing forces. Instead, loads on the temporary implant may reach a maximum of 10 kg, and more typically range from about 4 kg to about 5 kg. Furthermore, because the load bearing requirements for these temporary implants are significantly less than those needed for the traditional implants affixed in occlusal surfaces, the temporary implants only need to be inserted a very few millimeters into the bone. For example, traditional implants often are inserted approximately 5 mm into the occlusal surface of a maxillary or mandibular jawbone, whereas it is believed that a 2–3 mm implant insertion into the bone will provide a sufficient anchor for the temporary implants. In addition, because the temporary implant requires a significantly more shallow anchor depth, the implant may be removed relatively easily from the bone when the treatment period has ended.

Because a traditional occlusal surface implant is subjected to such large forces, a clinician must allow several months for the bone to thoroughly integrate around and into the surface of the implant before the implant may be used. However, because the inventive temporary implant is subjected to dramatically lower forces, significant bone integration usually is not required; and therefore, the temporary implant is available for use either immediately or within a very few weeks after insertion. Also, in order to achieve this bone integration, many traditional occlusal surface implants have an exterior surface which is highly porous or has other features to promote significant bone integration. And although the significant bone integration is required in order for such traditional implants to withstand the severe chewing forces, the bone integration makes it extremely difficult to remove such implants after treatment.

On the other hand, because of the relatively low forces exerted, the temporary implants of this invention require little to no bone integration, which is particularly advantageous in removing such implants after treatment. Whereas the traditional implants generally are made of materials designed to achieve some level of integration, the temporary implants do not have that limitation. Instead, the temporary implants are made of any material which is biocompatible and corrosion resistant. Typically, such implants are made of metal, ceramic, a bioresorbable material or a combination thereof. If metal is used, the metal typically is titanium, a titanium based alloy, a nickel-titanium based alloy, zirconium, a zirconium alloy, a stainless steel or a combination thereof. If a ceramic is used in forming the implant, the ceramic typically is aluminum oxide, titanium nitride, titanium dioxide, zirconium oxide, or a hydroxyl-apatite based ceramic such as calcium phosphate. In addition, a bioresorbable material such as poly L-lactate or a polyglycolic acid derivative may be used, either alone or in combination with various ceramic and/or metallic materials in forming the temporary implant. Because bioresorbable materials essentially "dissolve" over time, they may be used to advantage to form an implant which does not have to be removed after treatment.

In most cases, where little to no bone integration is desired, it is preferred to have a smooth bone-contacting outer body surface. In some instances, however, it may be desirable to have some level of bone integration, in which case a different surface material may be used. Also, the outer body surface may be chemically or mechanically treated to increase or decrease surface roughness and bone integration. For example, the temporary implant may be selectively coated with an osteoinductive factor to obtain accelerated bone growth and fixation along selected areas of the implant. Nonlimiting examples of osteoinductive factors include bone morphogenetic protein and growth hormone. If a mechanical surface treatment is desired, the temporary implant may be provided with an osteoconductive factor, which is any surface feature allowing bone to grow into the implant surface. For example, the implant may include surface regions which are roughened or porous or which have been coated with hydroxylapatite. If a porous surface is used, preferably the pore size ranges from about 100µ to about '500µ, more preferably from about 180µ to about 220µ.

In addition, the temporary implant may be coated with a material to inhibit or prevent infection. For example, the implant may be coated with an antibiotic or a basal laminar protein. If a basal laminar protein is used, it typically is coated onto the surfaces of the implant near the gum or palatal soft tissue. Such a coating stimulates adherence of soft tissue to the implant, thereby creating a biological seal to the oral cavity environment and preventing infectious agents from travelling into the bone.

Because the force placed on these temporary implants is significantly less than the force placed on traditional occlusal surface implants, the temporary implants may be made with smaller overall dimensions if desired. For example, for most applications, the length of the implant will range from about 2 mm to about 5 mm, and the diameter will range from about 0.5 mm to about 3 mm. A typical implant has a length of about 4 mm and a diameter of about 2 mm to about 2.5 mm. This ability to use an implant having dimensions which are smaller than those of traditional occlusal surface implants offers another significant benefit over such traditional implants. Because these traditional implants are large and are designed to be oriented in an occlusal surface, they only may be placed in the jawbone at a site where there is no tooth. However, in the vast majority of applications, the inventive temporary implant may be sized so as to fit easily between the roots of adjacent teeth when inserted into a lingual, buccal or labial surface of the maxillary or mandibular bone.

Figure 2:
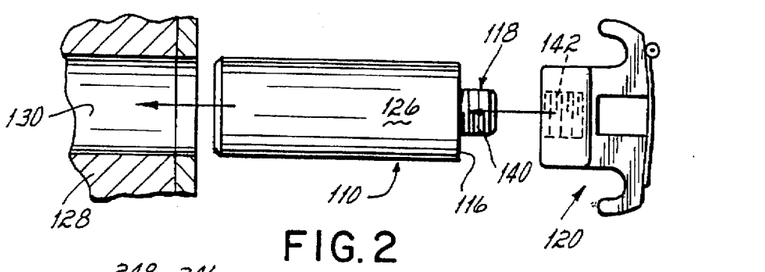
FIG. 2 shows an alternate embodiment of the temporary implant and corresponding orthodontic appliance.

Another embodiment of the temporary implant 110 is shown in FIG. 2. In this embodiment, the securing section 118 of the implant 110 is a threaded post 140 positioned at the outer end 116 of the implant 110, and the corresponding orthodontic appliance 120 includes a threaded bore 142 thereby allowing the appliance 120 to be releasably secured to the implant 110. In addition, the outer body surface 126 is substantially smooth.

Figure 3:
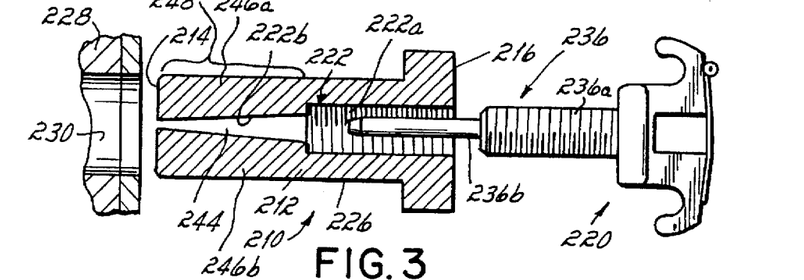
FIG. 3 shows another embodiment of the temporary implant of the invention.

Referring to FIG. 3, the implant 210 shown in this embodiment includes an outer body surface 226 which is generally smooth and contains no ridges. However, the longitudinal bore 222 in this implant 210 extends completely through the implant 210, from the outer end 216 to the inner end 214. Furthermore, the body portion 212 of the implant 210 includes a longitudinal cut 244 originating at the inner end 214 and extending part way along the length of the body 212. This embodiment includes a threaded cylindrical bore 222a having a uniform diameter which extends from the outer end 216 of the body 212 approximately half way down the length of the implant 210. At this point, the threaded bore 222a changes into a tapered bore 222b with a cross-sectional diameter which gets increasingly smaller toward the inner end 214 of the implant 210. The orthodontic appliance 220 corresponding with this implant includes a two-part fastening section 236 for releasably attaching the appliance 220 to the implant 210. The first part of the fastening section is a threaded post 236a, and the second part is a stem 236b which is integral with the threaded post 236a. Once the implant 210 is inserted into a hole 230 drilled in the bone 228, the orthodontic appliance 220 is threaded into the implant 210. As the appliance 220 is threaded in, the stem 236b forces the two halves 246a, 246b of the lower body 248 outward, thereby releasably securing the implant 210 to the bone.

Figures 4, 4A:
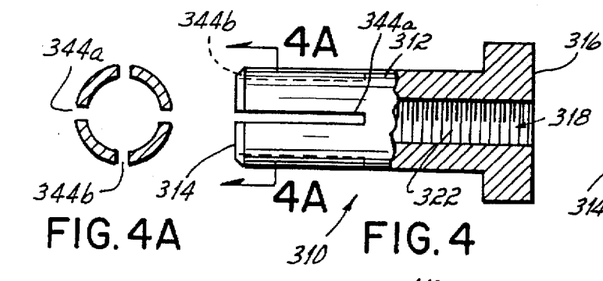
FIG. 4 shows yet another embodiment of a temporary implant formed of a shape-memory alloy and having four leg sections.
FIG. 4A is a cross-sectional view of the implant of FIG. 4 taken along line 4A—4A of FIG. 4.
Figure 4B:
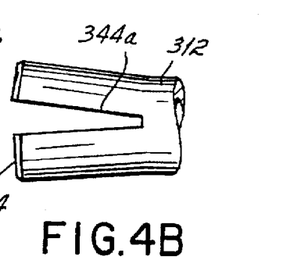
FIG. 4B is a partial view of the implant of FIG. 4 shown in deformed position.

If desired, the shape-memory effect of a nickel/titanium based alloy may be used to advantage in the temporary implant. For example, the temporary implant may be formed of a shape-memory alloy having a transformation temperature which is below the temperatures normally experienced in the mouth. In this fashion, an implant may be easily placed in a hole drilled in the bone while the implant is below its transformation temperature and in a generally martensitic state. Then, as the implant warms up to the temperatures in the mouth, the shape-memory alloy will cross its transformation temperature into austenitic phase and return to its predetermined shape which secures the implant in the bone socket. For example, this shape-memory effect can be used to effectively enlarge the outer diameter of the implant through expansion or bending of the implant. One example of an implant using a shape-memory alloy is shown in FIGS. 4, 4A and 4B. In this particular embodiment, a cylindrical bore 322 extends longitudinally from the outer end 316 to the inner end 314 of the implant 310, with the bore 322 being threaded from the outer end 316 to the middle of the body 312. In addition, the portion of the implant body 312 extending from the middle of the body 312 to the inner end 314 is formed of a shape-memory alloy which is treated to have a predetermined shape substantially as shown in FIG. 4B. The particular implant 310 shown includes two longitudinal cuts 344a, 344b extending into the body portion 312 of the implant 310 from the inner end 314, with the cuts being generally perpendicular to one another. The implant 310 is inserted into a hole in the bone at a temperature below the transformation temperature of the shape-memory alloy, so that the implant 310 has the configuration substantially as shown in FIG. 4, and may be pressed into the hole in the bone relatively easily. Once the shape-memory alloy warms above its transformation temperature, it returns to its original expanded shape substantially as shown in FIG. 4B, thereby securing the implant 310 into the bone.

Figure 5:
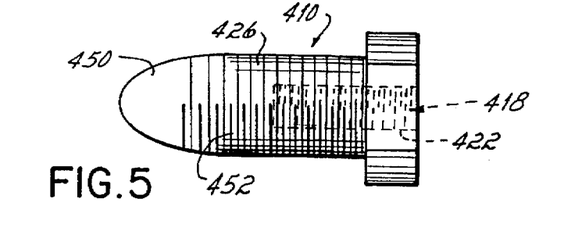
FIG. 5 illustrates another embodiment of the temporary implant in the shape of a tapered screw having threads.

As mentioned briefly above, the temporary implant may be of any particular shape as long as it is adapted to be temporarily affixed in a nonocclusal surface of the maxillary or mandibular bone. For example, the implant may have a cross-sectional shape other than a cylinder, and furthermore the diameter of the implant does not have to be uniform along its length. For example, the outer body surface of the implant may be conical in shape or may have sloped or tapered sidewalls which come together at the inner end of the implant. Referring to FIG. 5, a temporary implant 410 according to the principles of the invention is shown having tapered sidewalls 450. Furthermore, rather than having annular rings, a flat surface or some other surface formation, this particular embodiment has screw threads 452 on the outer body surface 426 allowing the implant 410 to be screwed into place in an opening in the maxillary or mandibular bone. Typically, a starter hole will be drilled into the bone prior to threading the implant into the opening. However, in certain embodiments, especially those that are conical in shape and small in diameter, it may be possible to insert the implant into the bone without initially drilling a hole.

Although the orthodontic appliance shown in FIGS. 1–3 is an orthodontic bracket, any of a number of different orthodontic appliances may be releasably attached to the inventive temporary implant as well. For example, instead of the orthodontic bracket shown, the particular orthodontic appliance may be a hook, ball joint, buccal tube, or any other orthodontic or orthopedic device which may benefit from the use of the temporary implant as an anchor in generating an orthodontic or orthopedic force in the mouth. A Herbst appliance and an arch-expanding jackscrew are just a few of the many additional types of devices which may be used with the temporary implant.

Figure 12:
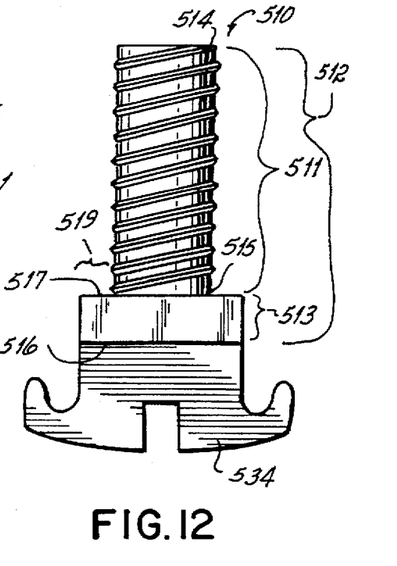
FIG. 12 shows a further embodiment of the temporary implant in which the implant and orthodontic appliance are formed as a single (i.e. integral) component.

Also, while the securing section and fastening section have been shown having corresponding threads for releasably attaching an appliance to the temporary implant, the appliance may be attached using any one of a number of different fastening devices. For example, the appliance may be snap-fit onto the implant or if desired, the appliance and implant may be formed as a single integral unit, although with this latter embodiment, the implant must be removed in order to change to a different orthodontic appliance. A version of the implant 510 having an integrally formed orthodontic appliance is shown in FIG. 12. As depicted, this particular embodiment includes an elongated body 512 having an in-bone portion 511 connected to an above-bone portion 513, with the in-bone and above-bone portions each having an inner and outer end (in-bone 514, 515; above-bone 516, 517). The cross-sectional area of the above-bone portion inner end 517 is greater than the cross-sectional area of the in-bone portion outer end 515, thereby forming a shoulder 519 having a bone-contacting surface on the above-bone portion inner end 517 capable of resting on a part of the bone surface adjacent to an opening in the bone when the implant is positioned in the mouth. The implant also includes an integrally formed orthodontic appliance, in this case, a bracket 534, extending from the above-bone portion 513 of the elongated body 512.

As mentioned briefly above, the temporary implant may be positioned anywhere along the palatal, lingual, buccal or labial surfaces of the maxillary or mandibular jawbones wherever a temporary anchor is needed in generating an orthodontic or orthopedic force. Furthermore, if desired, several temporary implants may be inserted in the mouth as needed. In some applications, the temporary implant may be used as an anchor to prevent tooth movement. For example, the insert may exert a force on a tooth that is countering another equal and opposite orthodontic force on that same tooth. In other applications, the temporary implant may be used to move a tooth or several teeth, in virtually any direction desired. In still other applications, the implant may be used to exert bone-to-bone, or orthopedic forces.

Figure 6:
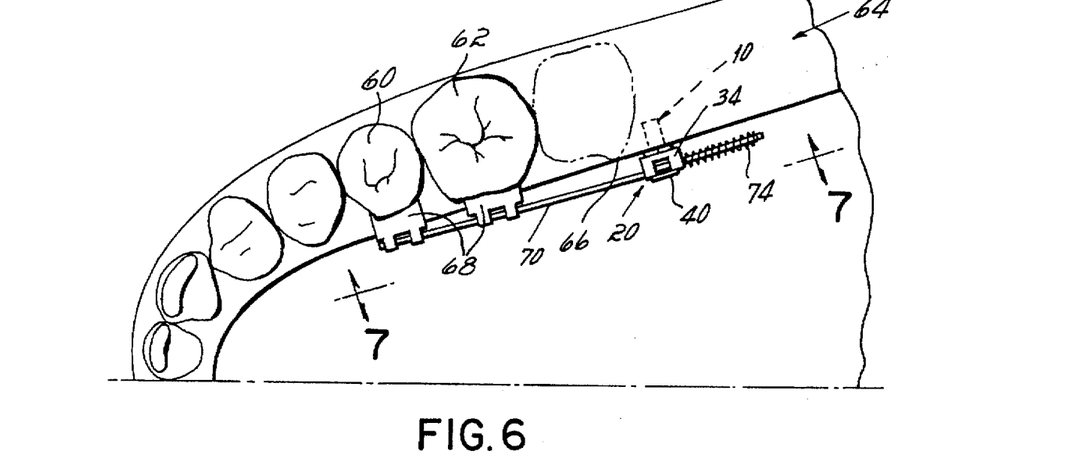
FIG. 6 is a top view of one half of the mandibular arch, showing a temporary implant of the invention implanted on the lingual surface adjacent the site of a missing third molar.
Figure 7:
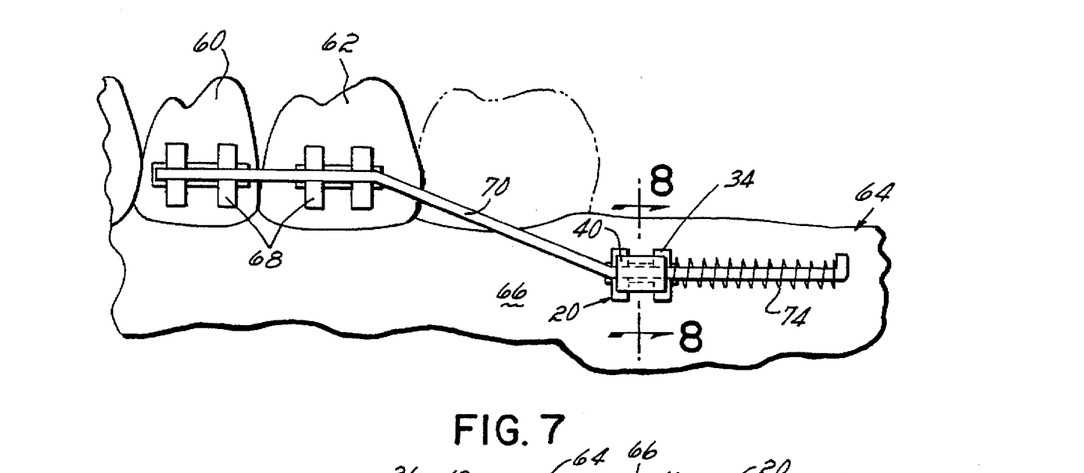
FIG. 7 is a side view taken along line 7—7 of FIG. 6.

As an example of an orthodontic application, referring to FIGS. 6–8, the temporary implant 10 of FIG. 1 is shown as an anchor in the distalization of the first and second molars 60, 62 on the right side of the mandibular jawbone 64. The temporary implant 10 is inserted into a hole 30 drilled in the lingual surface 66 of the mandibular bone 64 and a lingual bracket 34 having a fastening section (not shown) and a hinge cap 40 is releasably attached to the implant 10. In addition, a conventional lingual bracket 68 is affixed to each of the first and second molars 60, 62, and an archwire 70 is aligned in the archwire slot of each of the three brackets. In order to move the teeth distally, an expanding coil spring 74 is positioned on the archwire 70 distal to the temporary implant 10 and bracket 34 attached to the implant 10.

By way of example, the temporary implant also may be used to secure an "onplant" to a buccal, labial, lingual or palatal bone surface, thereby rendering the onplant available for substantially immediate use (i.e., on the order of minutes, hours, days or a few weeks after installation, depending upon the particular forces to be exerted on the implant). An "onplant" is a temporary orthodontic anchoring disk or plate having a bone-facing surface that is secured to bone using an osteoconductive factor such as hydroxylapatite which is disposed on at least part of the bone-facing surface. Details regarding the onplant may be found in Michael S. Block et al., "A New Device for Absolute Anchorage for Orthodontics", *American Journal of Orthodontics and Dentofacial Orthopedics*, pp. 251–258 (March, 1995), which is incorporated herein in its entirety by reference.

One of the limitations of the onplant is that it requires at least 10 to 12 weeks of healing time before it may be used. However, using the temporary implant of the present invention, the onplant may be made available for immediate use. For example, the onplant disk or plate may be formed with a hole or holes, i.e., a passage or passages, for receiving one or more of the inventive temporary implants, with the hole(s)/passage(s) typically generally perpendicular to the bone-facing surface. The implant then is passed through the hole in the onplant and into a hole formed in a bone surface, thereby securing the onplant for immediate use. In this application, the temporary implant preferably is made of a bioresorbable material. Therefore, although the implant provides sufficient strength, it "dissolves" over time, leaving only the onplant device secured to the bone surface by bone integration into the osteoconductive surfaces of the onplant disk.

Figure 9:
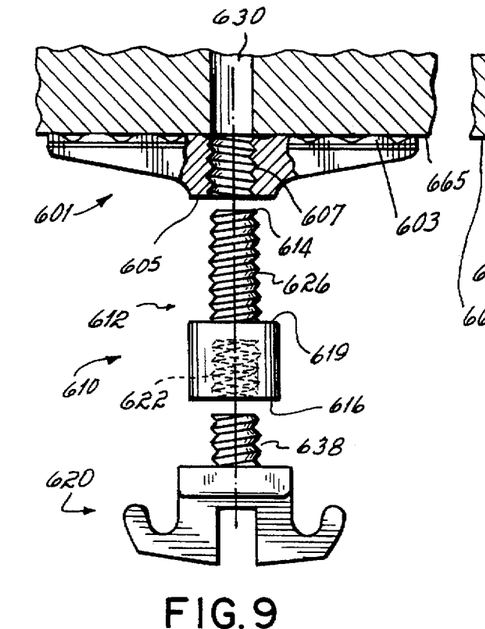
FIG. 9 is a partial cross section of an unassembled anchorage system including an onplant, an implant and orthodontic appliance, with the onplant aligned with an opening in a bone surface in the mouth.
Figure 10:
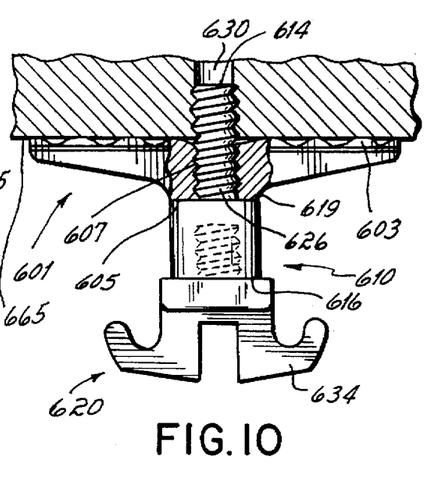
FIG. 10 is a partial cross section of the anchorage system of FIG. 9 in which the implant has been positioned through the onplant and secured in the bone surface opening, and the appliance has been attached to the implant.
Figure 11:
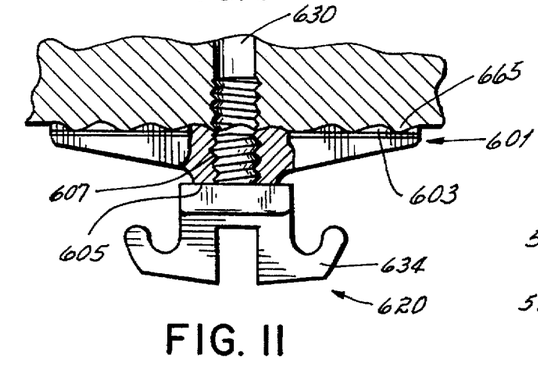
FIG. 11 is a partial cross section of the onplant and orthodontic appliance of FIGS. 9 and 10, in which the implant has been removed following integration of the bone surface into the onplant, and the orthodontic appliance has been threaded into a hole in the onplant.

With reference to FIGS. 9–11, a version of the anchorage system incorporating an onplant 601, an inplant 610 and an orthodontic appliance 620 is shown. As best seen in the exploded (i.e. unassembled) view shown in FIG. 9, the onplant 601 includes a bone-facing surface 603, an opposite face 605 and a hole 607 extending through the onplant 601, with the hole 607 being substantially perpendicular to the bone-facing surface 603 and opposite face 605. In this particular embodiment, the hole 607 is threaded so as to form a threaded cylindrical bore, and the bone-facing surface 603 may include an osteoconductive factor, such as hydroxylapatite, for example. The particular implant 610 shown includes an elongated body 612 having an inner end 614 and an outer end 616. The implant 610 also includes a threaded cylindrical post 626 for attaching the implant 610 to the onplant 601 and for securing the implant 610 in an opening in a bone surface. The implant 610 also includes a shoulder 619 which biases against the opposite face 605 of the onplant 601 when the two are secured together, as well as a securing section in the form of a threaded cylindrical bore 622, which is used for attaching an orthodontic appliance 620 to the implant 610. The particular orthodontic appliance 620 shown is a bracket 634 having a fastening section in the form of a threaded cylindrical post 638.

In use, the onplant 601 is positioned on a bone surface 665 in the mouth, and the inplant 610 is threaded through the onplant cylindrical bore 607 and positioned in an opening 630 in the bone surface 665. In this fashion, this aspect of the invention provides yet another anchorage system which is available for substantially immediate use, even though there has been no bone integration into the osteoconductive surface 603 of the onplant 601, as shown in FIGS. 9 and 10. With reference to FIG. 11, once the bone material has integrated into the osteoconductive surface 603 of the onplant 601 (as represented diagrammatically by the contour of the bone surface 665 now substantially following the rippled contour of the onplant bone-facing surface 603), the implant 610 may be removed, and an orthodontic appliance, for example a bracket 634, may be attached directly to the onplant 601.

The temporary implants of the present invention also may be used to exert a bone-moving force without having to transfer that force through the teeth. For example, when a patient has a regressive lower jaw, one of the traditional methods of treatment is to attach a Herbst appliance to the teeth. One end of the appliance is attached to a tooth extending down from the maxillary arch, and the other end of the Herbst appliance is attached to a mesially positioned tooth extending upward from the mandibular arch. Although this appliance moves the lower jaw forward, it has the undesirable effect of moving the teeth to which it is attached as well. With the inventive temporary implant, however, an implant may be positioned in each of the maxillary and mandibular arches, and the Herbst appliance may be connected directly to each of the implants, thereby generating a direct bone-to-bone force. Another illustration of the benefit of the inventive temporary implant is in the expansion of an arch. In one traditional method of arch expansion, a jackscrew is attached to four teeth on a given arch. The jackscrew then exerts an expanding force on the teeth, and the teeth translate this force to the bone, which has the undesirable effect of moving the teeth. With the temporary implants, the jackscrew may be attached directly to the implants temporarily affixed in the bone of the arch being expanded, thereby avoiding unwanted tooth movement.

While the temporary implant has been described in detail above with respect to a few embodiments and uses, the scope of the invention is to be determined by the following claims.

What is claimed is:

1. An implant for use with an orthodontic appliance the implant for use as an orthodontic or orthopedic load-bearing anchor in the mouth in creating a stabilizing or moving force, the implant comprising:

an elongated body having an in-bone portion connected to an above-bone portion, said in-bone portion and said avove-bone portion each having an inner and and an outer end, the cross sectional area of said above-bone portion inner end being greater than the cross-sectional area of said in-bone portion outer and, thereby forming a shoulder having a bone-contacting surface on said above-bone portion inner end capable of resting on a part of the bone surface adjacent to an opening in the bone when said implant is positioned in the mouth;

said elongated body further including a securing section for attaching an orthopedic appliance to said elongated body.

2. The implant of claim 1 wherein said securing section includes a threaded cylindrical bore extending from said above-bone portion outer end into said elongated body.

3. The implant of claim 2 wherein said in-bone portion includes an outer circumferential surface having screw threads.

4. The implant of claim 3 in combination with an orthodontic appliance having a fastening section, said fastening section including a threaded cylindrical post for engaging said threaded cylindrical bore.

5. The implant of claim 1 wherein said above-bone portion has a cross-sectional shape along at least a part of its length which is non-circular.

6. The implant of claim 5 wherein said non-circular shape includes at least one flat.

7. The implant of claim 1 wherein said securing section includes a threaded cylindrical post extending outward from said above-bone portion outer end.

8. The implant of claim 7 in combination with an orthodontic appliance having a fastening section, said fastening section including a threaded cylindrical bore for engaging said threaded cylindrical post.

9. The implant of claim 1 wherein said elongated body includes a bioresorbable material.

10. The implant of claim 1 wherein said elongated body includes an osteoinductive factor.

11. The implant of claim 1 wherein said elongated body includes an infection-inhibiting coating.

12. An implant including an orthopedic appliance, the implant for use as an orthodontic or orthopedic load-bearing anchor in the mouth in creating a stabilizing or moving force, the implant comprising:

an elongated body having an in-bone portion connected to an above-bone portion, said in-bone portion and said above-bone portion each having an inner end and an outer end, the cross-sectional area of said above-bone portion inner end being greater than the cross-sectional area of said in-bone portion outer end, thereby forming a shoulder having a bone-contacting surface on said above-bone portion inner end capable of resting on a part of the bone surface adjacent to an opening in the bone when said implant is positioned in the mouth;

said implant further including an integrally formed orthodontic appliance extending from said above-bone portion of said elongated body.

13. An implant for use with an orthodontic appliance, the implant for use as an orthodontic or orthopedic load-bearing anchor in the mouth in creating a stabilizing or moving force, the implant comprising:

an elongated body having an inner end, an outer end, a securing section for attaching an orthodontic appliance to said implant, and a retention portion for assisting in securing said implant within an opening in a bone surface in the mouth;

said retention portion including a section of the elongated body extending from one of said inner end and said outer end at least part-way toward the other of said inner end and said outer end, said retention portion further including a tapered bore and at least one longitudinal cut, said tapered bore and said longitudinal cut extending from said one of said inner and outer ends with said tapered bore having a cross-sectional area which gets smaller in the direction of said inner end, whereby when said implant is positioned in an opening in a bone surface of the mouth, and an orthodontic appliance having a corresponding fastening section is attached to said elongated body, a portion of the fastening section biases against a portion of the sidewall of said tapered bore and moves said retention portion radially outward thereby securing said implant in the opening in the bone surface.

14. The implant of claim 13 in combination with an orthodontic appliance having a fastening section, said fastening section including a stem sized so as to bias against a portion of the sidewall of said tapered bore and move said retention portion radially outward, thereby assisting in securing said implant in an opening in a bone surface.

15. The implant of claim 13 wherein said securing section includes a threaded cylindrical bore.

16. The implant of claim 15 in combination with an orthodontic appliance having a fastening section, said fastening section including a threaded cylindrical post corresponding with said threaded cylindrical bore, said fastening section further including a stem sized so as to bias against a portion of the sidewall of said tapered bore and move said retention portion radially outward, thereby assisting in securing said implant in an opening in a bone surface.

17. An implant for use with an orthodontic appliance, the implant for use as an orthodontic or orthopedic load-bearing anchor in the mouth in creating a stabilizing or moving force, the implant comprising:

an elongated body having an inner end, an outer end, a securing section for attaching an orthodontic appliance to said implant, and a retention portion for assisting in securing said implant within an opening in a bone surface in the mouth;

said retention portion including a section of the elongated body extending from one of said inner end and said outer end at least part-way toward the other of said inner end and said outer end, said retention portion being formed of a shape-memory alloy and including a bore and at least two longitudinal cuts, said bore and said longitudinal cuts extending from said one of said inner end and said outer end at least part-way toward said other of said inner end and said outer end, said longitudinal cuts forming at least two leg portions, said retention portion capable of assuming a predetermined shape in which said leg portions angle slightly radially outward when said retention portion reaches an ambient mouth temperature, thereby securing said implant in an opening in a bone surface in the mouth.

18. The implant of claim 17 wherein said securing section includes a threaded cylindrical bore extending from said outer end into said elongated body.

19. The implant of claim 18 in combination with an orthodontic appliance having a fastening section, said fastening section including a threaded cylindrical post for engaging said threaded cylindrical bore.

20. An anchorage system including an onplant and an implant for use as an orthodontic or orthopedic load-bearing anchor in creating a stabilizing or moving force in the mouth, the anchorage system comprising:

an onplant having a bone-facing surface, an opposite face, and a hole extending through said onplant at an angle substantially perpendicular to said bone-facing surface; and an implant for use in affixing said onplant to a bone surface in the mouth, said implant having an elongated body including an inner end and an outer end, a portion of said elongated body including said inner end capable of being positioned through said hole and in an opening in a bone surface in the mouth.

21. The anchorage system of claim 20 wherein said elongated body includes a shoulder, said shoulder capable of biasing against said opposite face of said onplant.

22. The anchorage system of claim 20 wherein said elongated body includes a securing section for attaching an orthodontic appliance to said implant.

23. The anchorage system of claim 22 wherein said securing section of said implant includes a threaded cylindrical bore.

24. The anchorage system of claim 23 in combination with an orthodontic appliance having a fastening section, said fastening section including a threaded cylindrical post for engaging said threaded cylindrical bore.

25. The anchorage system of claim 20 wherein said implant is made of a bioresorbable material.

26. A method of forming an orthodontic or orthopedic load-bearing anchor for use with an orthodontic appliance, the anchor being positioned in a non-occlusal surface of the mouth for use in creating a stabilizing or moving force, comprising the steps of:

providing an implant having an elongated body which includes an inner end, an outer end, an outer circumferential surface between said inner and outer ends, and a securing section for attaching an orthodontic appliance to said elongated body; and positioning at least a part of said elongated body, including said inner end, in an opening in a bone surface selected from the group consisting of the buccal, labial, lingual and palatal surfaces of the maxillary jawbone and the buccal, labial and lineal surfaces of the mandibular jawbone, thereby forming an anchor in a non-occlusal surface of the mouth for use in creating a stabilizing or moving force.

27. The method of claim 26 further including the step of attaching an orthodontic appliance to said implant.

28. The method of claim 27 wherein said securing section includes a threaded cylindrical bore and said orthodontic appliance includes a fastening section having a corresponding threaded cylindrical post, said attaching step including threading said post into said bore.

29. The method of claim 26 wherein said securing section is accessible at said outer end of said elongated body.

30. The method of claim 29 wherein said securing section includes a feature selected from the group consisting of a threaded cylindrical bore and a threaded cylindrical post.

31. The method of claim 26 further including the step of forming an opening in a bone surface selected from the group consisting of the buccal, labial, lingual and palatal surfaces of the maxillary jawbone and the buccal, labial and lingual surfaces of the mandibular jawbone prior to said positioning step.

32. The method of claim 26 wherein said elongated body includes an in-bone portion connected to an above-bone portion, said in-bone portion and said above-bone portion each having an inner end and an outer end, the cross-sectional area of said above-bone portion inner end being greater than the cross-sectional area of said in-bone portion outer end, thereby forming a shoulder having a bone-contacting surface on said above-bone portion inner end capable of resting on a part of the bone surface adjacent to an opening in the bone when said implant is positioned in the mouth;

said positioning step including inserting said in-bone portion into said opening in said bone surface, whereby said shoulder contacts the bone surface adjacent the mouth of said opening, said shoulder capable of distributing at least some force from said orthodontic appliance to the bone surface adjacent the mouth of said opening when an orthodontic appliance is attached to said implant.

33. The method of claim 26 wherein said elongated body includes a retention portion for assisting in securing said implant within the opening in the bone surface in the mouth.

34. The method of claim 33 wherein said retention portion includes a plurality of annular ridges positioned along said outer circumferential surface of said elongated body.

35. The method of claim 33 wherein said retention portion includes a section of the elongated body extending from one of said inner end and said outer end at least partway toward the other of said inner end and said outer end, said retention portion further including a tapered bore and at least one longitudinal cut, said tapered bore and said longitudinal cut extending from said one of said inner and outer ends with said tapered bore having a cross-sectional area which gets smaller in the direction of said inner end, whereby when said implant is positioned in the opening in the bone surface of the mouth, and an orthodontic appliance having a corresponding fastening section is attached to said elongated body, a portion of the fastening section biases against a portion of the sidewall of said tapered bore and moves said retention portion radially outward thereby securing said implant in the opening in the bone surface.

36. The method of claim 33 wherein said retention portion includes a section of the elongated body extending from one of said inner end and said outer end at least partway toward the other of said inner end and said outer end, said retention portion being formed of a shape-memory alloy and including a bore and at least two longitudinal cuts, said bore and said longitudinal cuts extending from said one of said inner end and said outer end at least part-way toward said other of said inner end and said outer end, said longitudinal cuts forming at least two leg portions, said retention portion assuming a predetermined shape in which said leg portions angle slightly radially outward when said retention portion reaches an ambient mouth temperature, thereby securing said implant in the opening in the bone surface in the mouth.

37. The method of claim 26 wherein said elongated body includes a bioresorbable material.

38. The method of claim 26 wherein said elongated body includes an osteoinductive factor.

39. The method of claim 26 wherein said elongated body includes an infection-inhibiting coating.

40. A method of forming an orthodontic or orthopedic load-bearing anchor including an orthodontic appliance in a non-occlusal surface of the mouth for use in creating a stabilizing or moving force, comprising the steps of:

providing an implant having an elongated body and an integrally formed orthodontic appliance, said elongated body including an inner end and an outer end; and positioning at least a part of said elongated body, including said inner end, in an opening in a bone surface selected from the group consisting of the buccal, labial, lingual and palatal surfaces of the maxillary jawbone and the buccal, labial and lingual surfaces of the mandibular jawbone, thereby forming an anchor in a non-occlusal surface of the mouth for use in creating a stabilizing or moving force.

41. A method of forming an orthodontic or orthopedic load-bearing anchorage system including an onplant and an inplant in the mouth for use in creating a stabilizing or moving force, comprising the steps of:

placing an onplant on a bone surface in the mouth selected from the group consisting of the buccal, labial, lingual and palatal surfaces of the maxillary jawbone and the buccal, labial and lingual surfaces of the mandibular jawbone, said onplant having a bone-facing surface, an opposite face, and a hole extending through said onplant at an angle substantially perpendicular to said bone-facing surface; and positioning a portion of an implant through said hole in said onplant and in an opening in said bone surface thereby affixing said onplant to said bone surface, said implant having an elongated body including an inner end and an outer end.

42. The method of claim 41 wherein said elongated body includes a shoulder, said shoulder biasing against said opposite face of said onplant.

43. The method of claim 41 wherein said elongated body includes a securing section for attaching an orthodontic appliance.

44. The method of claim 43 further including the step of attaching an orthodontic appliance.

45. The method of claim 41 wherein said implant includes an integrally formed orthodontic appliance.

46. The method of claim 41 wherein said hole includes a threaded cylindrical bore and said elongated body includes a threaded cylindrical post, said positioning step including threading said threaded cylindrical post into said threaded cylindrical bore.

* * * * *

UNITED STATES PATENT AND TRADEMARK OFFICE
CERTIFICATE OF CORRECTION

PATENT NO. : 5,697,779
DATED : December 16, 1997
INVENTOR(S) : Rohit Chaman Lal Sachdeva and Farrokh Farzin-Nia It is certified that error appears in the above-indentified patent and that said Letters Patent is hereby corrected as shown below:

Column 11, line 59, "appliance" should be --appliance,--
Column 11, line 65, "avov-bone" should be --above-bone--
Column 11, line 65, "inner and" should be --inner end--
Column 12, line 1, "outer and" should be --outer end--

Signed and Sealed this

Twenty-first Day of July, 1998

Attest:

BRUCE LEHMAN

Attesting Officer

Commissioner of Patents and Trademarks

(12) EX PARTE REEXAMINATION CERTIFICATE (7814th)
United States Patent
Sachdeva et al.

(10) Number: US 5,697,779 C1
(45) Certificate Issued: Oct. 19, 2010

(54) TEMPORARY IMPLANT FOR USE AS AN ANCHOR IN THE MOUTH

(75) Inventors: Rohit Chaman Lal Sachdeva, Plano, TX (US); Farrokh Farzin-Nia, Inglewood, CA (US)

(73) Assignee: Ormco Corporation, Orange, CA (US)

Reexamination Request:
No. 90/010,418, Feb. 18, 2009

Reexamination Certificate for:
Patent No.: 5,697,779
Issued: Dec. 16, 1997
Appl. No.: 08/480,836
Filed: Jun. 7, 1995

Certificate of Correction issued Jul. 21, 1998.

(51) Int. Cl.
*A61C 8/00* (2006.01)

(52) U.S. Cl. .............................. 433/2; 433/24; 433/173
(58) Field of Classification Search ...................... None
See application file for complete search history.

(56) References Cited

U.S. PATENT DOCUMENTS

| | | |
|---|---|---|
| 5,061,285 A | 10/1991 | Koch |
| 5,147,370 A | 9/1992 | McNamara et al. |
| 5,190,546 A | 3/1993 | Jervis |
| 5,219,287 A | 6/1993 | Nishihara |
| 5,290,289 A | 3/1994 | Sanders et al. |
| 5,356,431 A | 10/1994 | Pierce |
| 5,366,374 A | 11/1994 | Vlassis et al. |
| 5,387,213 A | 2/1995 | Breard et al. |
| 5,492,442 A | 2/1996 | Lasner |
| 5,545,165 A | 8/1996 | Biedermann et al. |
| 5,584,695 A | 12/1996 | Lal Sachdeva et al. |
| 5,588,838 A | 12/1996 | Hansson et al. |

FOREIGN PATENT DOCUMENTS

| | | |
|---|---|---|
| CH | 670 563 | 6/1989 |
| DE | 3535266 | 5/1986 |
| EP | 0180247 | 11/1985 |
| WO | PCT/NL91/00087 | 2/1992 |
| WO | 9214417 A1 | 9/1992 |

OTHER PUBLICATIONS

Frank J. Mogavero, Jr.; Titanium Endosseous Implants as Anchorage Units for Orthodontic Tooth Movement: An Experimental Study in the Dog; University of California Master of Science in Oral Biology Thesis; 1989; 72 pages.

American Association of Dental Research; Journal of Dental Research: Abstracts of Papers; vol. 68, p. 378; Mar. 1989; 2 pages.

Institut National De La Propriete Industrielle, Preliminary Search Report in corresponding FR19960006995, Jan. 30, 1998.

Block, Michael S., et al., "A new device for absolute anchorage for orthodontics", Am. J. Orthodontics and Dentofacial Orthopedics, Mar. 1995, pp. 251–258, vol. 107 No. 3. (8 pages).

Chen, PH.D., Jie et al., "Mechanical Response to Functional and Therapeutic Loading of A Retromolar Endosseous Implant Used for Orthodontic Anchorage to Mesially Translate Mandibular Molars", Implant Dentistry, Winter 1995, Copyright 1995 by Williams & Wilkins, pp. 246–258, vol. 4, No. 4. (14 pages).

Roberts, W. Eugene, "Remodeling of Mineralized Tissues, Part I: The Frost Legacy," Seminars in Orthodontics, Dec. 2006, pp. 216–237, vol. 12 No. 4. (22 pages).

(Continued)

*Primary Examiner*—Cary E. Wehner (57) ABSTRACT

This invention is directed to a temporary implant for use as an anchor in the mouth, as well as to a method of attaching the temporary implant to the maxillary or mandibular bone. The temporary implant includes an implant adapted to be temporarily affixed in a buccal, labial, lingual or palatal bone surface of the maxillary jawbone, or buccal, labial or lingual bone surface of the mandibular jawbone. In one embodiment, the implant includes a longitudinal threaded cylindrical bore for releasably attaching various orthodontic appliances to the implant.

OTHER PUBLICATIONS

Roberts, W. Eugene, "Remodeling of Mineralized Tissues, Part II: Control and Pathophysiology," Seminars in Orthodontics, Dec. 2006, pp. 238–253, vol. 12 No. 4. (16 pages).

Schneider, Paul M., et al., "Osseointegrated Implant Anchorage in a Growing Adolescent," Seminars in Orthodontics, Dec. 2006, pp. 272–283, vol. 12 No. 4. (12 pages).

Chang, Hwai–Nan, et al., "Bone–Screw Anchorage for Pendulum Appliances and Other Fixed Mechanics Applications," Seminars in Orthodontics, Dec. 2006, pp. 284–293, vol. 12 No. 4. (10 pages).

Roberts, W. Eugene, et al., "Miniature Implants and Retromolar Fixtures for Orthodontic Anchorage," Distraction Osteogenesis of the Facial Skeleton, Chapter 16, pub. date: Jan. 2007, pp. 205–214, vol. 205 No. 10. (10 pages).

Deguchi, T., et al., "The Use of Small Titanium Screws for Orthodontic Anchorage," Journal of Dental Research, 2003, pp. 377–381, vol. 82 No. 5. (5 pages).

Deguchi, Toru, et al., "Histomorphometric evaluation of alveolar bone turnover between the maxilla and the mandible during experimental tooth movement in dogs," American Journal of Orthodontics and Dentofacial Orthopedics, Jun. 2008, pp. 889–897. (9 pages).

Roberts, W. Eugene, "Bone Physiology, Metabolism, and Biomechanics in Orthodontic Practice," Orthodontics: Current Principles and Techniques, Chapter 6, 4th edition, pub. date: Apr. 2005, pp. 221–292, publisher Mosby, Incorporated. (72 pages).

Parr, J. Andrew, et al., "Sutural expansion using rigidly integrated endosseous implants: An experimental study in rabbits," The Angle Orthodontist, 1997, pp. 283–290, vol. 67 No. 4. (8 pages).

Roberts, W. Eugene, et al., "Osseous adaptation to continuous loading of rigid endosseous implants," American Journal of Orthodontics, Aug. 1984, pp. 95–111, vol. 86 No. 2. (17 pages).

Roberts, W. Eugene, et al., "Rate of mesial translation of mandibular molars using implant–anchored mechanics," The Angle Orthodontist, 1996, pp. 331–338, vol. 66 No. 5. (8 pages).

Roberts, W. Eugene, et al., "Rigid endosseous implants for orthodontic and orthopedic anchorage," The Angle Orthodontist, 1989, pp. 247–256, vol. 59 No. 4. (10 pages).

Roberts, W. Eugene, et al., "Rigid endosseous implant utilized as anchorage to protract molars and close an atrophic extraction site," The Angle Orthodontist, 1990, previously presented at the Biennial Meeting of the Edward H. Angle Society on Sep. 13, 1989, pp. 135–152, vol. 60 No. 2. (18 pages).

Roberts, W. Eugene, et al., "Implant–anchored orthodontics for partially edentulous malocclusions in children and adults," American Journal of Orthodontics and Dentofacial Orthopedics, Sep. 2004, pp. 302–304, vol. 126 No. 3. (3 pages).

James D. Christoff, Letter and attachment from 3M Innovative Properties Company to Patent Owner Ormco Corporation, dated Feb. 24, 2009. (11 pages).

Triaca, et al., "A Net Titanium Flat Screw Implant for Orthodontic Anchoring onto the Anterior Palate," Informationen Aus Orthodontie Und Kief, 1992, pp. 251–257, vol. 24. (10 pages).

Robert, W. Eugene, "Bases Physiologiques De la Reaction Osseuse Aux Implants Dentaires" (translated as "Physiological Bases of the Bone Reaction to Dental Implants"), Reportage: Premiere Renconte Internationale D'Implantogie Et Des Biomateriaux De Rouen, Mar. 21, 22, 23, 1991 (translated as Report: First International Meeting on Implantology and Biomaterials, Rouen, Mar. 21, 22, 23, 1991), L'Information Dentaire, Jun. 6, 1991, pp. 1795, 1797, vol. 73, No. 22. (6 pages).

Smalley, Ward M., et al., "Osseointegrated titanium implants for maxillofacial protraction in monkeys," Am. J. Orthod. Dentofac. Orthop., Oct. 1988, pp. 285–295, vol. 94 No. 4. (11 pages).

Gainsforth, B.L., et al., "A Study of Orthodontic Anchorage Possibilities in Basal Bone," American Journal of Orthodontics & Dentofacial Orthopedics (formerly known as American Journal of Orthodontics and Oral Surgery), Aug. 1945, vol. 31 Issue 8, pp. 406–417. (12 pages).

Joseph E. Kovarik, Letter from Rocky Mountain Orthodontics to Patent Owner Ormco Corporation, dated Oct. 16, 2008. (3 pages).

David L. De Briun, Letter and attachments from Patent Owner Ormco Corporation to Rocky Mountain Orthodontics, dated Nov. 19, 2008. (3 pages).

Joseph E. Kovarik, Letter from Rocky Mountain Orthodontics to Patent Owner Ormco Corporation, dated Dec. 19, 2008. (3 pages).

Brett A. Hesterberg, Letter and exhibits from Dentaurum J.P. Winkelstoeter KG to Patent Owner Ormco Corporation, dated Nov. 3, 2008. (49 pages).

David L. De Briun, Letter from Patent Owner Ormco Corporation to Dentaurum J.P. Winkelstoeter KG, dated Dec. 3, 2008. (3 pages).

Brett A. Hesterberg, Letter from Dentaurum J.P. Winkelstoeter KG to Patent Owner Ormco Corporation, dated Dec. 19, 2008. (2 pages).

Roberts, W. Eugene, et al., Osseus Adaptation To Continuous Loading Of Rigid Endosseous Implants, Am. J. Orthod., Aug. 1984, pp. 95–111, vol. 86, No. 2. (17 pages).

Higuchi, Kenji W., and James M. Slack. "The Use Of Titanium Fixtures For Intraoral Anchorage To Facilitate Orthodontic Tooth Movement," The Int'l J. of Oral & Maxillofactial Implants, 1991, pp. 338–344, vol. 6, No. 3. (7 pages).

Roberts, W. Eugene, The Implant Bone Interface and Orthodontic Applications, Prosthetic Impressions, Summer 1990, pp. 1–2, vol. 1, No. 2. (2 pages).

Roberts, W. E., et al., "Bone physiology of orthodontics: Metabolic and mechanical control mechanisms," Symposion der Deutschen Gessellschaft fur Kieferorthopadie, Bad Homburg, 1989, pp. 33–55. (32 pages).

Roberts, W. Eugene, "Bone Tissue Interface," Journal of Dental Education, 1988, pp. 804–809, vol. 52, No. 12. (6 pages).

Roberts, W. Eugene, "Bone Tissue Interface," Int. J. Oral Implant., 1988, pp. 71–74, vol. 5, No. 1. (4 pages).

Zingheim, William, "Implantologists Meet in Chicago," Dentistry Today, Oct. 1987, pp. 41. (2 pages).

Roberts, W. Eugene, et al., "Bone physiology and metabolism," CDA Journal, Oct. 1987, pp. 54–61. (8 pages).

Helm, et at., "Bone Remodeling Response to Loading of Rigid Endosseous Implants," J. Dent. Res. 66 (Special Issue) 1987, p. 186. (1 page).

Roberts, W. E., et at., "Development of Rigid Osseous Interface with Tricalcium Phosphate (TCP)–coated Endosseous Implants," J. Dent. Res. 65 (Special Issue) 1986, p. 347. (1 page).

Turley, et al., "Titanium Endosseous and Vitallium Subperfosteal Implants As Orthodontic Anchors for Tooth Movement in Dogs.," IADR Abstracts, 1984, p. 344. (1 page).

Roberts, W. Eugene, "Rigid endosseous anchorage and tricalcium phosphate (TCP)–coated implants," CDA Journal, Dec. 1984, pp. 158–161. (4 pages).

Nichols, Owen, "Frontiers in orthodontic research". PCSO Bulletin 56(2), 1984, pp. 58–59. (2 pages).

Roberts, W. E., et al., "Bone Modeling and Remodeling Response to Load Applied via Rigid Endosseous Implants," IADR Abstracts, 1983, p. 27. (1 page).

Arbuckle, Gordon R., et al., "Osseointegrated Implants and Orthodontics," Oral and Maxillofacial Surgery Clinics of North America, Nov. 1991, pp. 903–919, vol. 3, No. 4. (17 pages).

Roberts, W. Eugene, et al., "Bone Physiological Principles Applied to Orthodontics and Dentofacial Orthopedics," Mechanical and Biological Basics in Orthodontic Therapy, 1991, pp. 21–29. (7 pages).

Roberts, W. Eugene, et al., "Interface Histology of Rigid Endosseous Implants," J. Oral Implant., 1986, pp. 406–416, vol. 12. (11 pages).

Robert, W. Eugene, "Bases Physiologiques De la Reaction Osseuse Aux Implants Dentaires," Premiere Rencontre Internationale D'Implantologie Et Des Biomateriaux De Rouen, L'Information Dentaire, Jun. 6, 1991, pp. 1795, 1797, vol. 73, No. 22. (3 pages).

Roberts, W. Eugene, et al., "Physiology of Osseous and Fibrous Integration," AO, 1992, pp. 57–60, vol. 85 Scientific. (4 pages).

Roberts, W. Eugene, et al., "Bone Physiology And Metabolism In Dental Implantology: Risk Factors For Osteoporosis And Other Metabolic Bone Diseases," Implant Dentistry, Spring 1992, pp. 11–21, vol. 1, No. 1. (11 pages).

Roberts, W. Eugene, et al., "Endosseous Implants For Rigid Orthodontic Anchorage," Modern Practice in Orthognathic and Reconstructive Surgery, 1992, pp. 1231–1263, vol. 2. (35 pages).

Roberts, W. Eugene, et al., "Principles of Orthodontic Biomechanics: Metabolic and Mechanical Control Mechanisms," U. of Michigan Ctr. Human G&D Monograph #27 Craniofacial Growth Series, 1992, pp. 189–255. (68 pages).

Roberts, W. Eugene, "Management of Edentulous Space in the Lower Posterior Segment," Decision Making in Dental Treatment Planning. (Eds) Mosby Year Book, 1993, pp. 146–149. (4 pages).

Roberts, W. Eugene, et al., "Bone Physiology and Metabolism," Contemporary Implant Dentistry, Mosby Year Book, 1993, pp. 327–353. (29 pages).

Roberts, W. Eugene, "Bone Physiology, Metabolism, and Biomechanics in Orthodontic Practice," Graber and Vanarsdall: Orthodontics: Current Principles and Techniques, 2nd ed., Mosby–Yearbook, 1994, pp. 193–234. (41 pages).

Hohlt, W. F., et al., "Rigid implants for orthodontic anchorage," The Biological Mechanisms of Tooth Eruption, Resorption and Replacement by Implants, 1994 Harvard Society for the Advancement of Orthodontics, 1994, pp. 661–666. (6 pages).

Roberts, W. Eugene, "The use of dental implants in orthodontic therapy," The Biological Mechanisms of Tooth Eruption, Resorption and Replacement by Implants, 1994 Harvard Society for the Advancement of Orthodontics, 1994, pp. 631–642. (12 pages).

Roberts, W. E., et al., "Orthodontics as a Restorative Option," Orthodontic Dialogue, Fall 1994, pp. 2–4, vol. 7, No. 1. (4 pages).

Roberts, W. Eugene, et al., "Rigid Implant Anchorage to Close a Mandibular First Molar Extraction Site," Journal of Clinical Orthodontics, Dec. 1994, pp. 693–704, vol. XXVIII, No. 12. (13 pages).

Garetto, Lawrence P., et al., "Remodeling Dynamics of Bone Supporting Rigidly Fixed Titanium Implants: A Histomorphometric Comparison in Four Species Including Humans," Implant Dentistry, 1995, pp. 235–243, vol. 4 No. 4. (9 pages).

Roberts, W. Eugene, "Adjunctive Orthodontic Therapy in Adults Over 50 Years of Age: Clinical Management of Compensated, Partially Edentulous Malocclusion," Indiana Dental Association Journal, Summer 1997, pp. 33–34, 36–38, 40–41. (9 pages).

Sander, Franz Martin, et al., "Bending Properties of Superelastic Nickel Titanium Archwires," Journal of Clinical Orthodontics, Oct. 2008, pp. 581–586, vol. XLII No. 10. (8 pages).

Roberts, W. Eugene, et al., "Remodeling of Devitalized Bone Threatens Periosteal Margin Integrity of Endosseous Titanium Implants with Threaded or Smooth Surfaces:Indications for Provisional Loading and Axially Directed Occlusion," Indiana Dental Association Journal, Jul./Aug. 1989, pp. 19–24, vol. 68 No. 4. (6 pages).

Roberts, W. Eugene, et al., "Multidisciplinary Management of Congential and Acquired Compensated Malocclusions Diagnosis, Etiology and Treatment Planning", Indiana Dental Association Journal, Summer 1996, pp. 42–43, 45–48, 50–51. (9 pages).

Roberts, W. Eugene, et al., "Bone Physiology And Biomechanics Of Implant Anchorage: Closing Atrophic Endentulous Spaces," 2007 Moyer Symposium, USA, Craniofacial Growth Series, 2008, pp. 51–110 (in original), pp. 1–60, vol. 45. (60 pages).

Roberts, W. Eugene, et al., "Implant Anchorage And Tissue Engineering: Broadening The Scope Of Orthodontics And Dentofacial Orthopedics," 2005 Moyer Symposium, USA, Craniofacial Growth Series, 2005, pp. 1–39, vol. 42. (39 pages).

Roberts, W. Eugene, "Introduction: Bone Physiology in Orthodontics," Seminars in Orthodontics, Jun. 2004, pp. 99, vol. 10 No. 2. (1 page).

Roberts, W. Eugene, et al., "Bone development and function: Genetic and environmental mechanisms," Seminars in Orthodontics, Jun. 2004, pp. 100–122, vol. 10 No. 2. (23 pages).

Roberts, W. Eugene, et al., "Bone Modeling: Biomechanics, Molecular Mechanisms, and Clinical Perspectives," Seminars in Orthodontics, Jun. 2004, pp. 123–161, vol. 10 No. 2. (39 pages).

Huja, Sarandeep S., et al., "Mechanism of Osseointegration:Characterization of Supporting Bone with Indentation Testing and Backscattered Imaging," Seminars in Orthodontics, Jun. 2004, pp. 162–173, vol. 10 No. 2. (12 pages).

Yip, Gary, et al., "Micro–Computed Tomography: High Resolution Imaging of Bone and Implants in Three Dimensions," Seminars in Orthodontics, Jun. 2004, pp. 174–187, vol. 10 No. 2. (14 pages).

An article entitled "A New Titanium Flat Screw Implant for Orthodontic Anchoring onto the Anterior Palate" (translated from the orginal German publication entitled "Ein neues Titan–Flachschrauben–Implantat zur orthodontischen Verankerung am anterioren Gaumen") by Albino Triaca et al. ("Triaca et al."), published on pp. 251–257 in the vol. 24, 1992 edition of *Information Aus Orthodontie Und Kief*.

An article entitled "Orthodontic Force Application to Titanium Endosseous Implants" by Turley et al. ("Turley et al."), published on pp. 151–162 in the Apr. 1988 edition of *The Angle Orthodontist*.

An article entitled "The Possibility of Skeletal Anchorage" by Thomas D. Creekmore and Michael K. Eklund ("Creekmore et al."), published on pp. 266–269 in the Apr. 1983 issue (vol. XVII, No. 4) of the *Journal of Clinical Orthodontics*.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 29 is cancelled.

Claims 26, 31, 32 and 40 are determined to be patentable as amended.

Claims 27, 33 and 34, dependent on an amended claim, are determined to be patentable.

New claims 47-68 are added and determined to be patentable.

Claims 1-25, 28, 30, 35-39 and 41-46 were not reexamined.

26. A method of forming an orthodontic or orthopedic load-bearing anchor for use with an orthodontic appliance, the anchor being positioned in a non-occlusal surface of the mouth for use in creating a stabilizing or moving force, comprising the steps of:

providing an implant having an elongated body which includes an inner end, an outer end, an outer circumferential surface between said inner and outer ends, and a [securing section for attaching] *projecting portion extending outwardly from said outer end, said projecting portion configured to mechanically attach* an orthodontic appliance to said elongated body; and positioning at least a part of said elongated body, including said inner end, in an opening in a bone surface selected from the group consisting of the buccal, labial, lingual and palatal surfaces of the maxillary jawbone and the buccal, labial and [lineal] *lingual* surfaces of the mandibular jawbone, thereby forming an anchor in a non-occlusal surface of the mouth for use in creating a stabilizing or moving force; *said elongated body directly engaging the maxillary or mandibular jawbone.*

31. The method of claim 26 further including the step of forming [an] *the* opening in [a] *the* bone surface selected from the group consisting of the buccal, labial, lingual and palatal surfaces of the maxillary jawbone and the buccal, labial and lingual surfaces of the mandibular jawbone prior to said positioning step.

32. [The ] *A* method of [claim 26] *forming an orthodontic or orthopedic load-bearing anchor for use with an orthodontic appliance, the anchor being positioned in a non-occlusal surface of the mouth for use in creating a stabilizing or moving force, comprising the steps of:*

*providing an implant having an elongated body which includes an inner end, an outer end, an outer circumferential surface between said inner and outer ends, and a securing section for attaching an orthodontic appliance to said elongated body; and*

*positioning at least a part of said elongated body, including said inner end, in an opening in a bone surface selected from the group consisting of the buccal, labial, lingual and palatal surfaces of the maxillary jawbone and the buccal, labial and lingual surfaces of the mandibular jawbone, thereby forming an anchor in a non-occlusal surface of the mouth for use in creating a stabilizing or moving force;*

*wherein said elongated body includes an in-bone portion connected to an above-bone portion, said in-bone portion and said above-bone portion each having an inner end and an outer end, the cross-sectional area of said above-bone portion inner end being greater than the cross-sectional area of said in-bone portion outer end, thereby forming a shoulder having a bone-contacting surface on said above-bone portion inner end capable of resting on a part of the bone surface adjacent to an opening in the bone when said implant is positioned in the mouth;*

*said positioning step including inserting said in-bone portion into said opening in said bone surface, whereby said shoulder contacts the bone surface adjacent the mouth of said opening, said shoulder capable of distributing at least some force from said orthodontic appliance to the bone surface adjacent the mouth of said opening when an orthodontic appliance is attached to said implant.*

40. A method of forming an orthodontic or orthopedic load-bearing anchor including an orthodontic appliance in a non-occlusal surface of the mouth for use in creating a stabilizing or moving force, comprising the steps of:

providing an implant having an elongated body and an integrally formed orthodontic appliance, said elongated body including an inner end and an outer end; and positioning at least a part of said elongated body, including said inner end, in an opening in a bone surface selected from the group consisting of the buccal, labial, lingual and palatal surfaces of the maxillary jawbone and the buccal, labial and lingual surfaces of the mandibular jawbone, *said elongated body directly engaging the maxillary or mandibular jawbone,* thereby forming an anchor in a non-occlusal surface of the mouth for use in creating a stabilizing or moving force.

*47. The method of claim 26, wherein positioning at least a part of said elongated body, including said inner end, in an opening in a bone surface includes positioning in the buccal surface of the maxillary jawbone.*

*48. The method of claim 26, wherein positioning at least a part of said elongated body, including said inner end, in an opening in a bone surface includes positioning in the labial surface of the maxillary jawbone.*

*49. The method of claim 26, wherein positioning at least a part of said elongated body, including said inner end, in an opening in a bone surface includes positioning in the lingual surface of the maxillary jawbone.*

*50. The method of claim 26, wherein positioning at least a part of said elongated body, including said inner end, in an opening in a bone surface includes positioning in the palatal surface of the maxillary jawbone.*

*51. The method of claim 26, wherein positioning at least a part of said elongated body, including said inner end, in an opening in a bone surface includes positioning in the buccal surface of the mandibular jawbone.*

*52. The method of claim 26, wherein positioning at least a part of said elongated body, including said inner end, in an opening in a bone surface includes positioning in the labial surface of the mandibular jawbone.*

53. The method of claim 26, wherein positioning at least a part of said elongated body, including said inner end, in an opening in a bone surface includes positioning in the lingual surface of the mandibular jawbone.

54. The method of claim 26, wherein the elongated body has a threaded portion.

55. The method of claim 54, wherein positioning at least a part of said elongated body, including said inner end, in an opening in a bone surface includes screwing said threaded portion in said bone surface.

56. The method of claim 55, wherein screwing said threaded portion into said bone surface includes screwing said threaded portion through tissue and into said bone surface.

57. The method of claim 40, wherein positioning at least a part of said elongated body, including said inner end, in an opening in a bone surface includes positioning in the buccal surface of the maxillary jawbone.

58. The method of claim 40, wherein positioning at least a part of said elongated body, including said inner end, in an opening in a bone surface includes positioning in the labial surface of the maxillary jawbone.

59. The method of claim 40, wherein positioning at least a part of said elongated body, including said inner end, in an opening in a bone surface includes positioning in the lingual surface of the maxillary jawbone.

60. The method of claim 40, wherein positioning at least a part of said elongated body, including said inner end, in an opening in a bone surface includes positioning in the palatal surface of the maxillary jawbone.

61. The method of claim 40, wherein positioning at least a part of said elongated body, including said inner end, in an opening in a bone surface includes positioning in the buccal surface of the mandibular jawbone.

62. The method of claim 40, wherein positioning at least a part of said elongated body, including said inner end, in an opening in a bone surface includes positioning in the labial surface of the mandibular jawbone.

63. The method of claim 40, wherein positioning at least a part of said elongated body, including said inner end, in an opening in a bone surface includes positioning in the lingual surface of the mandibular jawbone.

64. The method of claim 40, wherein the elongated body has a threaded portion.

65. The method of claim 64, wherein positioning at least a part of said elongated body, including said inner end, in an opening in a bone surface includes screwing said threaded portion in said bone surface.

66. The method of claim 65, wherein screwing said threaded portion into said bone surface includes screwing said threaded portion through tissue and into said bone surface.

67. A method of forming an orthodontic or orthopedic load-bearing anchor for use with an orthodontic appliance, the anchor being positioned in a non-occlusal surface of the mouth for use in creating a stabilizing or moving force, comprising the steps of:

providing an implant having an elongated body which includes an inner end, an outer end defining an above-bone portion, an outer circumferential surface between said inner and outer ends, and a recessed portion extending from above-bone portion of said outer end toward said inner end, said recessed portion configured to mechanically attach an orthodontic appliance to said elongated body; and positioning at least a part of said elongated body, including said inner end, in an opening in a bone surface selected from the group consisting of the buccal, labial, lingual and palatal surfaces of the maxillary jawbone and the buccal, labial and lingual surfaces of the mandibular jawbone, thereby forming an anchor in a non-occlusal surface of the mouth for use in creating a stabilizing or moving force; said elongated body directly engaging the maxillary or mandibular jawbone.

68. A method of forming an orthodontic or orthopedic load-bearing anchor for use with an orthodontic appliance, the anchor being positioned in a non-occlusal surface of the mouth for use in creating a stabilizing or moving force, comprising the steps of:

providing an implant having an elongated body which includes an inner end, an outer end, an outer circumferential surface between said inner and outer ends, and a securing section;

positioning at least a part of said elongated body, including said inner end, in an opening in a bone surface selected from the group consisting of the buccal, labial, lingual and palatal surfaces of the maxillary jawbone and the buccal, labial and lingual surfaces of the mandibular jawbone, thereby forming an anchor in a non-occlusal surface of the mouth for use in creating a stabilizing or moving force; said elongated body directly engaging the maxillary or mandibular jawbone; and snap-fitting an orthodontic appliance to said securing section to releasably attach said orthodontic appliance to said implant.

\* \* \* \* \*